(12) United States Patent
Cheng

(10) Patent No.: US 11,963,774 B2
(45) Date of Patent: Apr. 23, 2024

(54) METHOD PROBE WITH HIGH DENSITY ELECTRODES, AND A FORMATION THEREOF

(71) Applicant: International Business Machines Corporation, Armonk, NY (US)

(72) Inventor: Kangguo Cheng, Albany, NY (US)

(73) Assignee: International Business Machines Corporation, Armonk, NY (US)

( * ) Notice: Subject to any disclaimer, the term of this patent is extended or adjusted under 35 U.S.C. 154(b) by 846 days.

(21) Appl. No.: 15/838,557

(22) Filed: Dec. 12, 2017

(65) Prior Publication Data
US 2019/0175039 A1 Jun. 13, 2019

(51) Int. Cl.
*A61B 5/24* (2021.01)
*A61B 5/00* (2006.01)
*H01L 21/768* (2006.01)
*H01L 27/12* (2006.01)

(52) U.S. Cl.
CPC .......... *A61B 5/24* (2021.01); *H01L 21/76898* (2013.01); *A61B 2562/0285* (2013.01); *A61B 2562/046* (2013.01); *H01L 27/1203* (2013.01)

(58) Field of Classification Search
CPC ... A61B 5/24; A61B 2562/028; A61B 5/0031; A61B 5/7264; A61B 5/369; A61B 8/54; H01L 2224/48227; H01L 27/14632; H01L 27/14687; H01L 27/14692; H01L 2924/1433; H01L 21/8249; H01L 29/41741; H01L 29/41766; H01L 29/456; H01L 29/66712; H01L 29/7809; H01L 41/0477

See application file for complete search history.

(56) References Cited

U.S. PATENT DOCUMENTS

| 6,440,793 B1* | 8/2002 | Divakaruni ....... H01L 27/10841 |
| | | 438/243 |
| 8,261,428 B2 | 9/2012 | Fang et al. |
| 8,355,768 B2 | 1/2013 | Masmanidis et al. |
| 2009/0325424 A1 | 12/2009 | Aarts et al. |
| 2011/0054583 A1* | 3/2011 | Litt .................... A61B 5/14552 |
| | | 607/116 |

(Continued)

FOREIGN PATENT DOCUMENTS

| CN | 104053786 B | 6/2017 |
| EP | 3151908 A1 | 4/2017 |

(Continued)

OTHER PUBLICATIONS

Kwong et al. "Vertical Silicon Nanowire Platform for Low Power Electronics and Clean Energy Applications" Journal of Nanotechnology vol. 2012, Article ID 492121, 21 pages (May 2011). (Year: 2011).*

(Continued)

*Primary Examiner* — Joseph A Stoklosa
*Assistant Examiner* — Brian M Antiskay
(74) *Attorney, Agent, or Firm* — L. Jeffrey Kelly

(57) ABSTRACT

A high-density electrode array, a neural probe, and a method of control thereof, the high-density electrode array including a plurality of neural electrodes, a wordline, and a bitline where each neural electrode of the plurality of neural electrodes is individually controlled by the wordline and the bitline.

6 Claims, 9 Drawing Sheets

(56) References Cited

U.S. PATENT DOCUMENTS

| | | | | |
|---|---|---|---|---|
| 2013/0072775 A1* | 3/2013 | Rogers | ............... | A61M 5/31 |
| | | | | 600/378 |
| 2013/0134546 A1* | 5/2013 | Cheng | ............... | A61B 5/24 |
| | | | | 257/506 |
| 2014/0166981 A1* | 6/2014 | Doyle | ............... | H01L 29/7827 |
| | | | | 257/24 |
| 2015/0005610 A1* | 1/2015 | Zhang | ............... | A61B 5/688 |
| | | | | 600/391 |
| 2016/0128588 A1 | 5/2016 | Melosh et al. | | |
| 2017/0231518 A1 | 8/2017 | Dayeh et al. | | |

FOREIGN PATENT DOCUMENTS

| | | | |
|---|---|---|---|
| WO | WO 2013/016343 | A1 | 1/2013 |
| WO | 2015191628 | A1 | 12/2015 |
| WO | 2015193674 | A1 | 12/2015 |

OTHER PUBLICATIONS

Chen et al. "A CMOS-Compatible Poly-Si Nanowire Device with Hybrid Sensor/Memory Characteristics for System-on-Chip Applications". Sensors 2012, 12, 3952-3963. Mar. 2012. (Year: 2012).*

Micheloni et al. "Architectural and Integration Options for 3D NAND Flash Memories". Computers 2017, 6(3), 27. Aug. 2017. (Year: 2017).*

Mel, et al. "The NIST Definition of Cloud Computing". Recommendations of the National Institute of Standards and Technology: Nov. 16, 2015.

Ruther et al., "New approaches for CMOS-based devices for large-scale neural recording", 2014 (see p. 3) https://arxiv.org/ftp/arxiv/papers/1706/1706.10058.pdf.

* cited by examiner

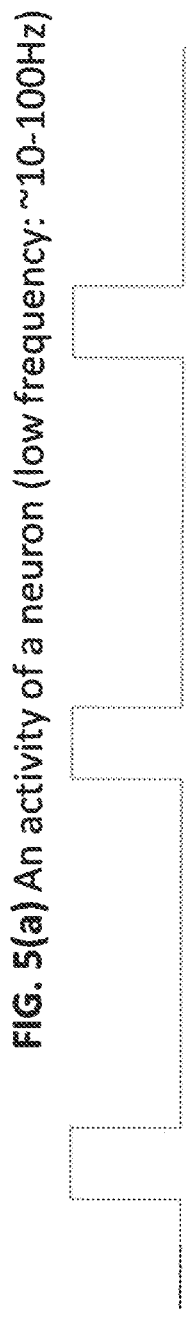
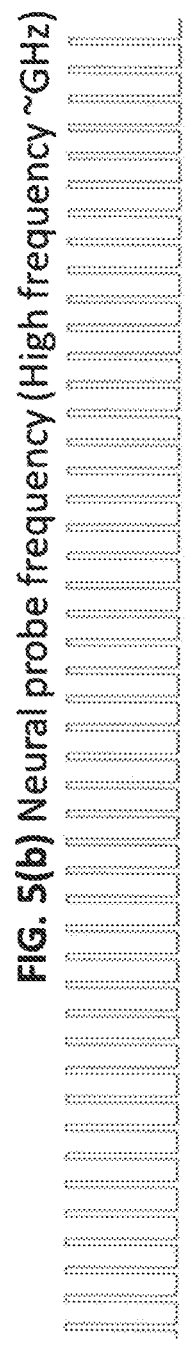
FIG. 5(a) An activity of a neuron (low frequency: ~10-100Hz)
FIG. 5(b) Neural probe frequency (High frequency ~GHz)

METHOD PROBE WITH HIGH DENSITY ELECTRODES, AND A FORMATION THEREOF

BACKGROUND

The present invention relates generally to a method and structure for forming neural probe with high density electrodes, and more particularly, but not by way of limitation, to a method and structure to form a neural probe with high-density electrodes which are formed on top of an array of vertical transistors.

Neural probes are useful in neural science such as for monitoring/stimulating neurons. Neuron density of a brain is in the range of million to hundreds of millions of neurons per cubic millimeter. It is highly desired to have neural probes with high-density electrodes so that a large amount of data on brain activity can be collected in a timely manner.

However, the conventional neuron probes have a limited number of electrodes, which results in the conventional neuron probes being unsuitable for a comprehensive study of brain activity.

SUMMARY

In an exemplary embodiment, the present invention can provide a high-density electrode array, the array including a plurality of neural electrodes, a wordline, and a bitline, where each neural electrode of the plurality of neural electrodes is individually connected to the wordline and the bitline.

One or more other exemplary embodiments include a computer program product and a system.

Other details and embodiments of the invention will be described below, so that the present contribution to the art can be better appreciated. Nonetheless, the invention is not limited in its application to such details, phraseology, terminology, illustrations and/or arrangements set forth in the description or shown in the drawings. Rather, the invention is capable of embodiments in addition to those described and of being practiced and carried out in various ways and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Aspects of the invention will be better understood from the following detailed description of the exemplary embodiments of the invention with reference to the drawings, in which FIG. 1 exemplarily depicts an individual neural electrode 100 according to an embodiment of the present invention;

FIGS. 5(a) and 5(b) exemplarily depict a second method of control of the neural probe 300 according to an embodiment of the present invention;

DETAILED DESCRIPTION

Figure 1:
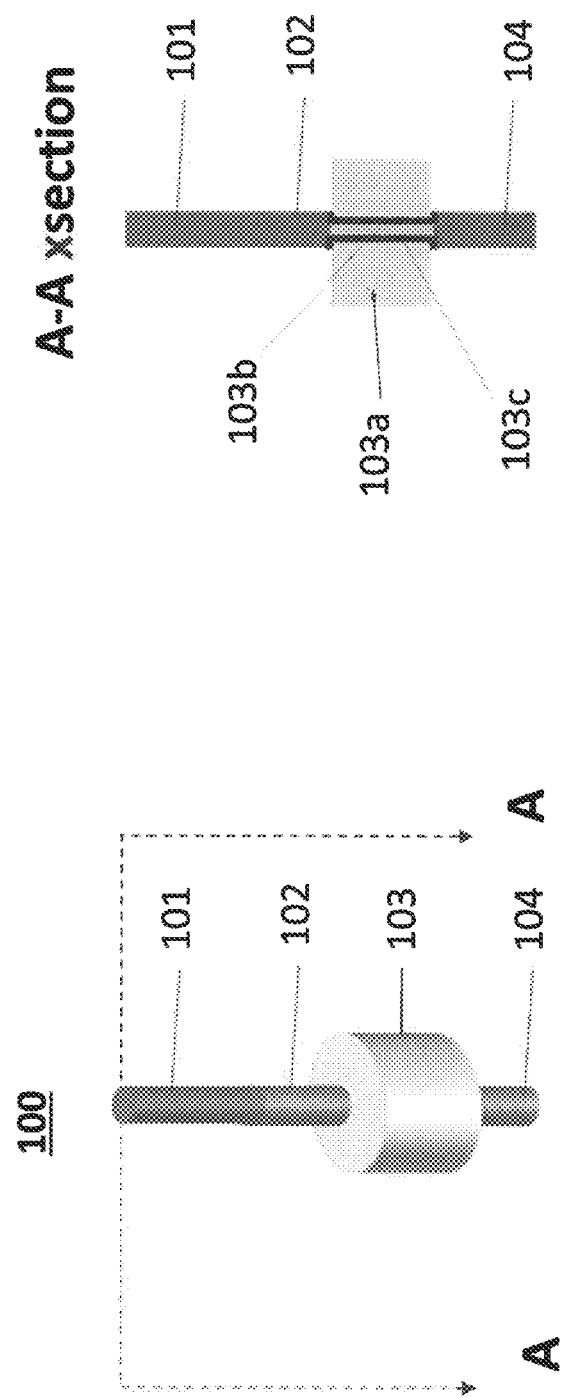

The invention will now be described with reference to FIG. 1-9, in which like reference numerals refer to like parts throughout. It is emphasized that, according to common practice, the various features of the drawing are not necessarily to scale. On the contrary, the dimensions of the various features can be arbitrarily expanded or reduced for clarity.

With reference now to the example depicted in FIG. 1, the individual neural electrode 100 includes an electrode 101 connected to a vertical transistor. In some embodiments, the vertical transistor is a vertical nanowire transistor with a top drain 102, a bottom source 104, and a gate 103 wrapping around the nanowire channel 105. The individual neural electrode 100 is electrically connected to drain 102. The gate may comprise a gate conductor 103a and a gate dielectric 103b. The gate dielectric 103b is placed between the gate conductor 103a and the channel 103c. The gate dielectric 103b may comprise any suitable dielectric, including but not limited to silicon oxide, silicon nitride, silicon oxynitride, high-k materials (k stands for relative dielectric constant), or any combination of these materials. Examples of high-k materials include but are not limited to metal oxides such as hafnium oxide, hafnium silicon oxide, hafnium silicon oxynitride, lanthanum oxide, lanthanum aluminum oxide, zirconium oxide, zirconium silicon oxide, zirconium silicon oxynitride, tantalum oxide, titanium oxide, barium strontium titanium oxide, barium titanium oxide, strontium titanium oxide, yttrium oxide, aluminum oxide, lead scandium tantalum oxide, and lead zinc niobate. The high-k may further include dopants such as lanthanum, aluminum, magnesium. Note that source and drain are interchangeable. The source and drain are typically doped semiconductor materials such as silicon, silicon germanium, and germanium. Dopants can be n-type or p-type dopants. In some embodiments, the source/drain may be wider than the nanowire channel to reduce the parasitic resistance in some embodiments, the source/drain may comprise metallic conductive materials, including but not limited to tungsten, cobalt, titanium, titanium nitride, tantalum nitride, a silicide, or any suitable combination of those materials. The structure may further comprise other elements that are not shown for clarity. For example, dielectric spacers may be formed between gate and source/drain. The nanowire channel may comprise any suitable semiconductor materials, including but not limited to, silicon, silicon germanium, germanium, III-V compound semiconductor, II-V compound semiconductor, carbon nanotube, etc. In some embodiments, the vertical transistor is a vertical fin-type transistor. The electrode 100 is electrically connected to the top drain. It can be formed during contact and/or wiring in the back end of line (BEOL) of the conventional complementary metal-oxide-semiconductor (CMOS).

Figure 2:
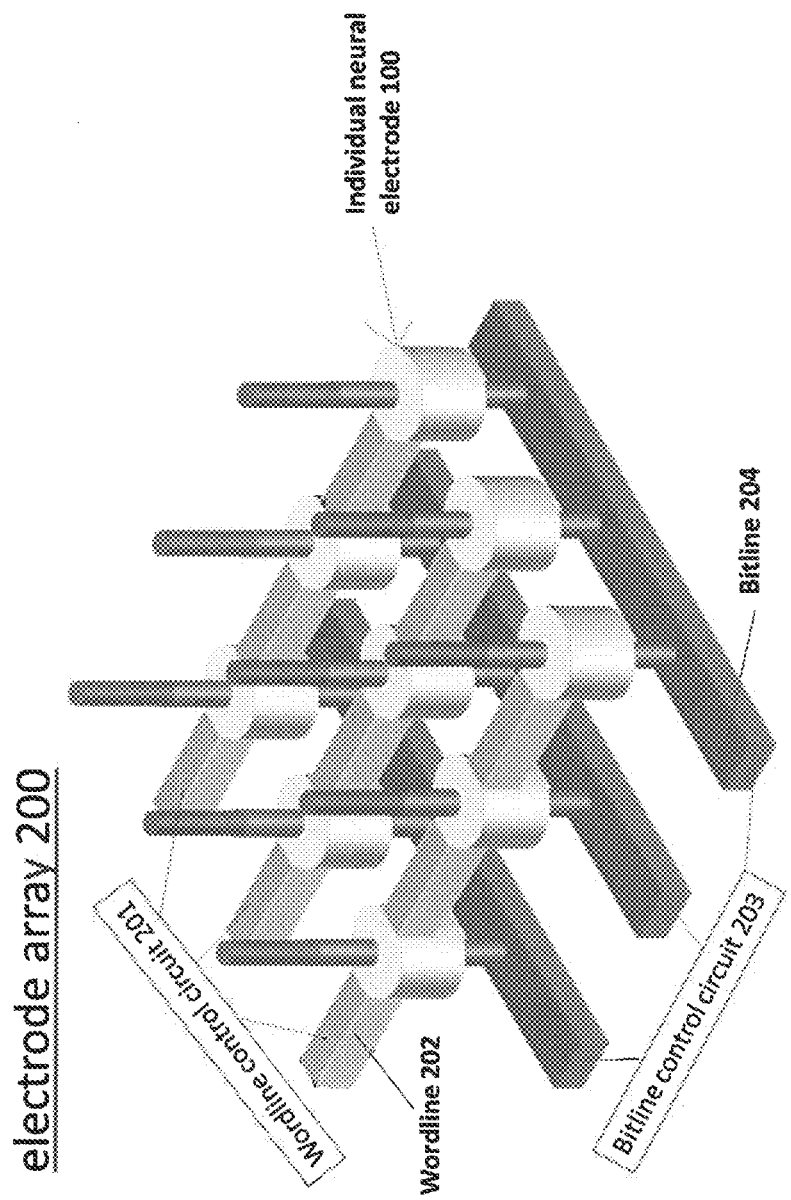
FIG. 2 exemplarily depicts an electrode array 200 including the individual neural electrode 100 according to an embodiment of the present invention.

As shown in FIG. 2, an electrode array 200 may be formed which includes a plurality of the individual neural electrodes 100. A 3×3 array is exemplarily shown in FIG. 2 Multiple neural electrodes 100 form on top of an array of vertical field effect transistors (FETs). Each neural electrode 100 connects to a vertical nanowire FET with a wrap-around gate. The array of VFET has individually addressable wordline 202 and bitline 204. Each neural electrode 100 can be individually addressed by wordline control circuits 201 and bitline control circuits 203 for sensing/stimulating. One electrode (e.g., cell) may be at each intersection of a bitline and a wordline. That is, a high-density electrode array 200 can be fabricated along with the conventional vertical transistor CMOS on the same chip. Therefore, sensing, stimulating, and data processing can be done by the same chip. The array of vertical transistors has a cross-bar type bitline 204 and wordline 202 so that each electrode 100 can be individually addressed. Each gate 103 of each electrode 100 can be controlled by the wordline voltage. As a result, one can use each individual electrode to monitor/stimulate brain activity. The control circuits may further comprise sensing circuits or electrically connected to sensing circuits.

Figure 3:
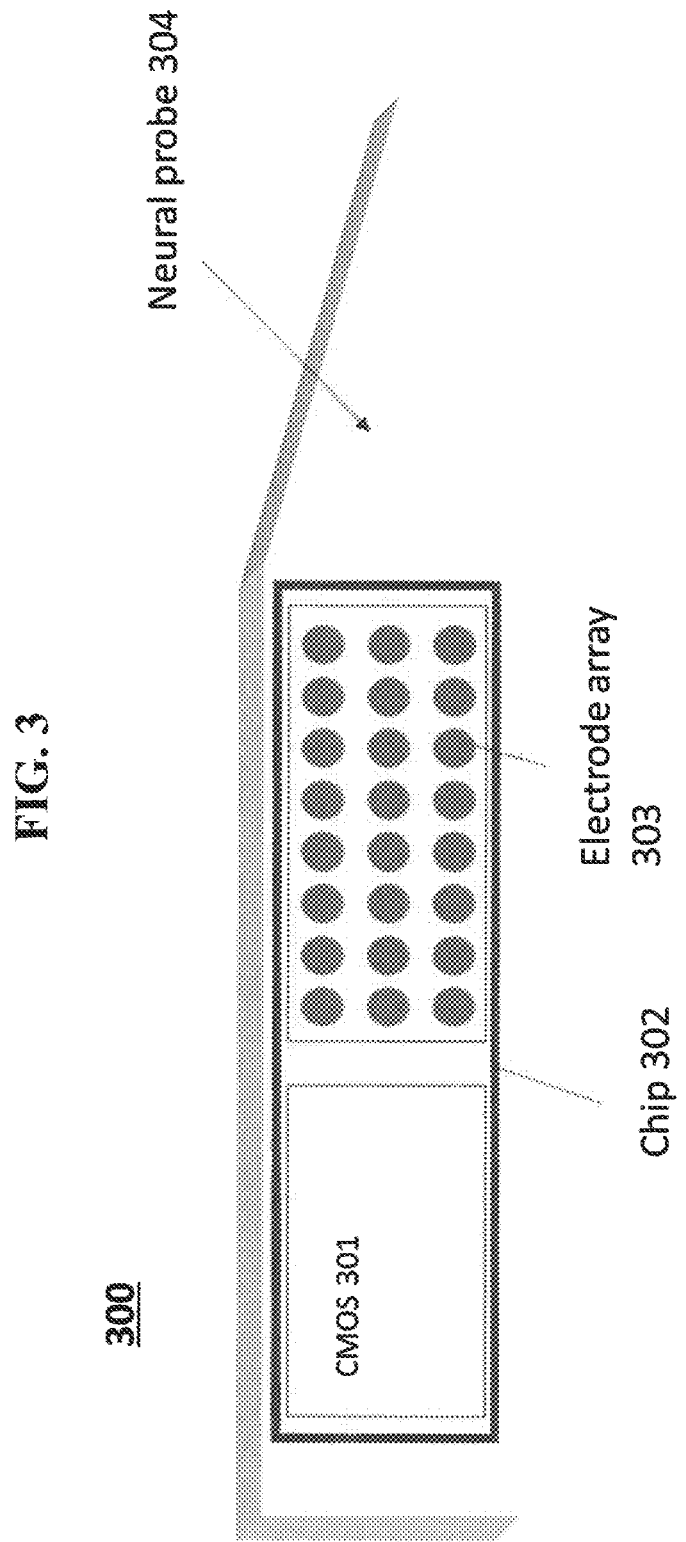
FIG. 3 exemplarily depicts a neural probe 300 according to an embodiment of the present invention.

FIG. 3 exemplarily depicts a neural probe apparatus 300. The neural probe apparatus 300 includes a chip 302 with high-density electrode array 303 (i.e., the electrode array 200 as depicted in FIG. 2) and a complementary metal-oxide-semiconductor (CMOS) 301 processor can be mounted on a neural probe 304. That is, since the vertical transistor electrodes 100 are fully compatible with CMOS fabrication, they can be built along with data storage circuit (memory) and data processing circuit (logic) on the same chip (e.g., CMOS 301). In the depicted embodiment, a sheer volume of brain activity can be in-situ monitored/stimulated/processed.

Figure 6:
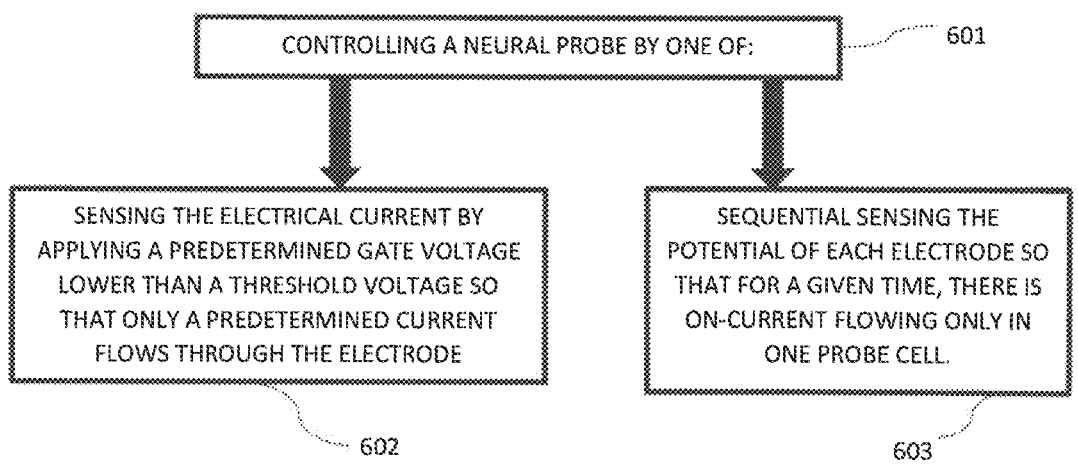
FIG. 6 exemplarily shows a high-level flow chart for a control method 600 of the neural probe 300.

With reference now to FIG. 6, a method 600 can control the neural probe apparatus 300. As shown in at least FIG. 7, one or more computers of a computer system 12 according to an embodiment of the present invention can include a memory 28 having instructions stored in a storage system to perform the steps of FIG. 6.

Although one or more embodiments (see e.g., FIGS. 7-9) may be implemented in a cloud environment 50 (see e.g., FIG. 8), it is nonetheless understood that the present invention can be implemented outside of the cloud environment.

Figure 4:
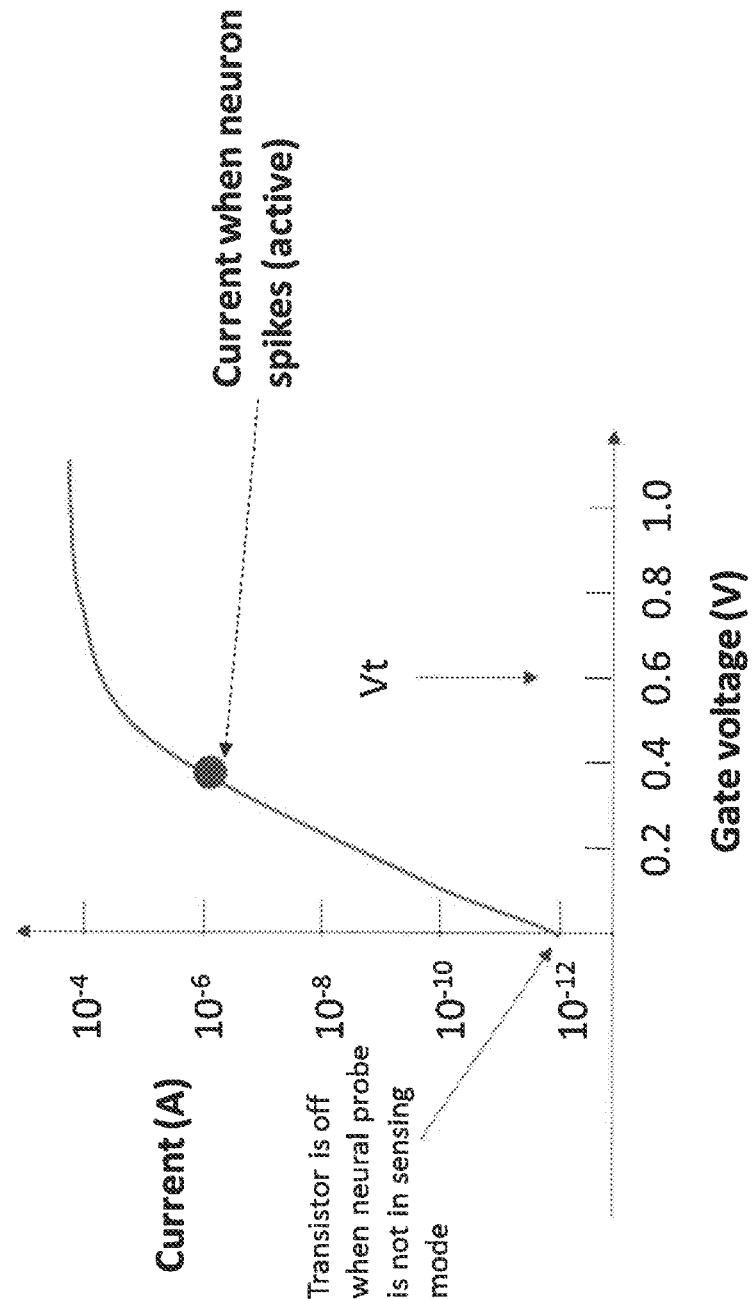
FIG. 4 exemplarily depicts a first method of control of the neural probe 300 according to an embodiment of the present invention.

Referring generally to FIGS. 4-6, the method 600 can avoid overheating of the brain during operation of the neural probe apparatus 300 (i.e., step 601) by, in a first solution (i.e., step 602), sensing the electrical current by applying a small gate voltage (lower than the threshold voltage (Vt)) so that only a small current flows through the electrode. By reducing the current, the joule heating is reduced and thus overheating of brain is avoided. In other words, the sub-threshold current is used for sensing in this invention. We refer this sensing scheme as subthreshold sensing because the vertical transistor is operated in the subthreshold regime (i.e., gate voltage below the threshold voltage of the transistor).

FIG. 4 exemplarily depicts a source current (e.g., through the electrode) vs. gate voltage schematics for the neural probe apparatus 300. The current (Y-axis) is in log scale and the gate voltage is in linear scale. For example, the transistor has a Vt of 0.6V. The transistor is off when the neural probe 300 is not in the sensing mode. Thus, no current is flowing through the transistor and a gate voltage is zero. When sensing, 0.36V voltage is applied to the gate (i.e., current when neuron spikes (active). 0.36V is lower than the threshold voltage of 0.6V, so the transistor is biased in so-called "subthreshold" mode. The source voltage can be zero. If a neuron connected to a probe is active, the electrical potential of the electrode changes, equivalent to changing the source-drain voltage of the transistor, resulting a current flow through the transistor. If the neuron is inactive, the electrode potential is zero, equivalent to zero source-drain bias, so no current flows through the transistor. In the example below, when a neuron become active, the current is about $1\times10^{-6}$ ampere (A) (low enough to avoid overheating but high enough to be detected).

In step 603, sequential sensing of the potential of each electrode is performed so that for a given time, there is on-current flowing only in one neural probe in an array. The rationale is that human brain functions at a frequency of 10s or 100s Hz. As shown in FIGS. 5(a) and 5(b), the inventive neuron sensor can operate readily at GHz (Gigahertz). Therefore, by cycling sensing through an array of probe electrodes, the sensor can still capture neuron activity. Shown in FIG. 5(a) is a schematic of an activity of a neuron (low frequency: ~10-100 Hz) and in FIG. 5(b), a neural probe frequency (High frequency ~GHz). Sequential sensing means that a neuron activity is not always monitored. Instead, a group of neurons (e.g., 1,000) are sensed sequentially (meaning the sensing cycles through 1,000 neurons). However, because the inventive nano-neural array can be operated in a much higher frequency (e.g., GHz) than the brain activity frequency (e.g., 10-100 Hz), most neuron activity can still be picked up by the sensor. For example, assuming the neuron activity frequency of 100 Hz, the neural probe array operated at 1 GHz (1 billion Hz). 1,000 neurons in an array are sensed sequentially. Thus, in every second a given neuron will be sensed 1 million (1 billion/1,000) times in a second, frequently enough to capture most neuron activities.

Therefore, with the inventive high-density electrode neural probe 300 and control thereof, the percentage of the neurons that can be sensed at same time increases significantly.

Note that solution 1 and solution 2 can be implemented independently, even though they can be used in combination.

Sensing is used to describe the invention. This invention can also be used to stimulate neurons in a brain. In the application of stimulation, wordline is used to turn on the vertical transistors in the same wordline. Meanwhile, voltage or current can be applied to bitline. Voltage potential or current reaches to the neural electrode connected to the vertical transistor and stimulates neurons. In the application of stimulating neuron, sometimes a voltage higher than the threshold voltage of the vertical transistor is desired. If so, one can still use solution 2 (sequential stimulating) to enable each individual neural probe to stimulate neurons while avoiding overheating the brain.

Exemplary Aspects, Using a Cloud Computing Environment

Although this detailed description includes an exemplary embodiment of the present invention in a cloud computing environment, it is to be understood that implementation of the teachings recited herein are not limited to such a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client circuits through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 7:
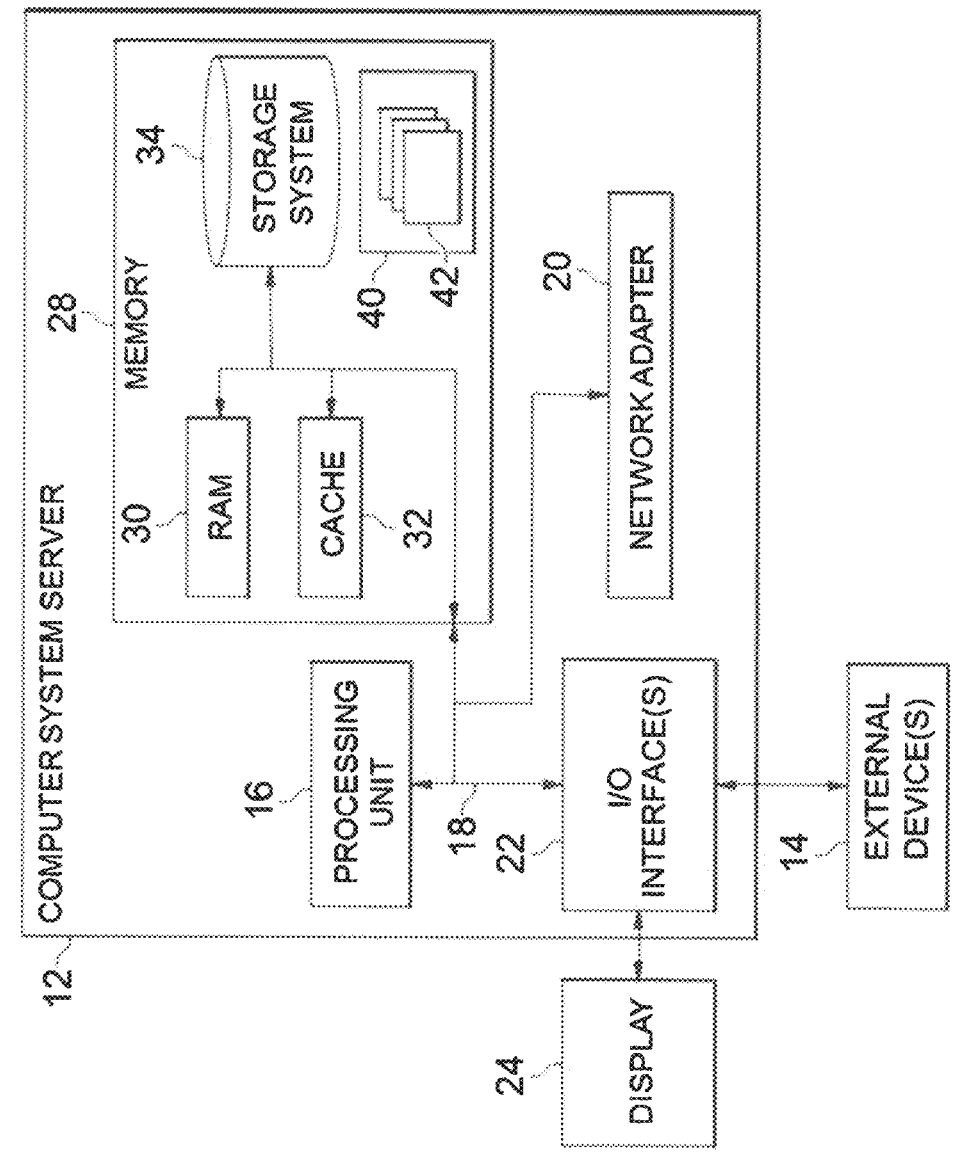
FIG. 7 depicts a cloud computing node 10 according to an embodiment of the present invention.

Referring now to FIG. 7, a schematic of an example of a cloud computing node is shown. Cloud computing node 10 is only one example of a suitable node and is not intended to suggest any limitation as to the scope of use or functionality of embodiments of the invention described herein. Regardless, cloud computing node 10 is capable of being implemented and/or performing any of the functionality set forth herein.

Although cloud computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

Referring again to FIG. 7, computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external circuits 14 such as a keyboard, a pointing circuit, a display 24, etc.; one or more circuits that enable a user to interact with computer system/server 12; and/or any circuits (e.g., network card, modem, etc.) that enable computer system/server 12 to communicate with one or more other computing circuits. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Figure 8:
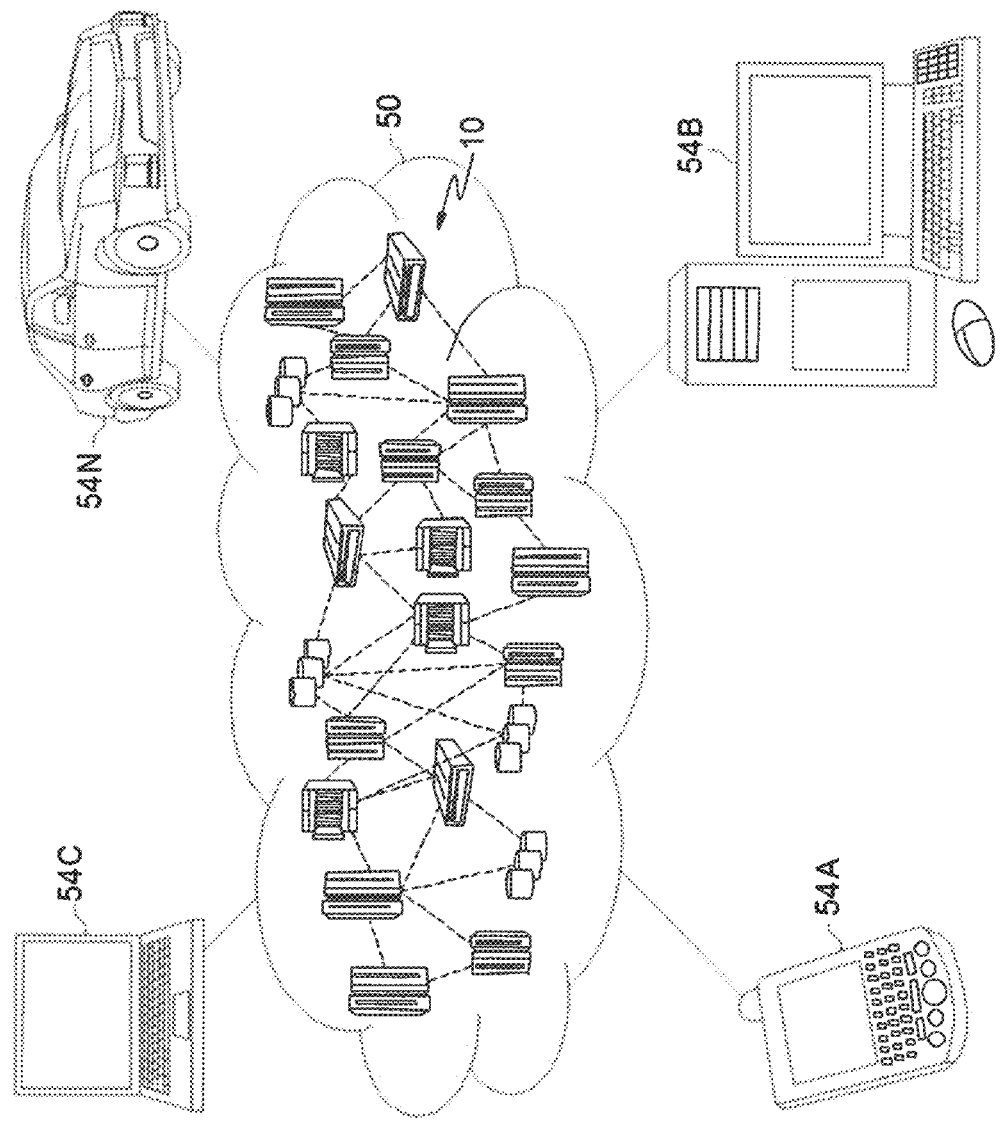
FIG. 8 depicts a cloud computing environment 50 according to an embodiment of the present invention.

Referring now to FIG. 8, illustrative cloud computing environment 50 is depicted. As shown, cloud computing environment 50 comprises one or more cloud computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing circuit. It is understood that the types of computing circuits 54A-N shown in FIG. 8 are intended to be illustrative only and that computing nodes 10 and cloud computing environment 50 can communicate with any type of computerized circuit over any type of network and/or network addressable connection (e.g., using a web browser).

Figure 9:
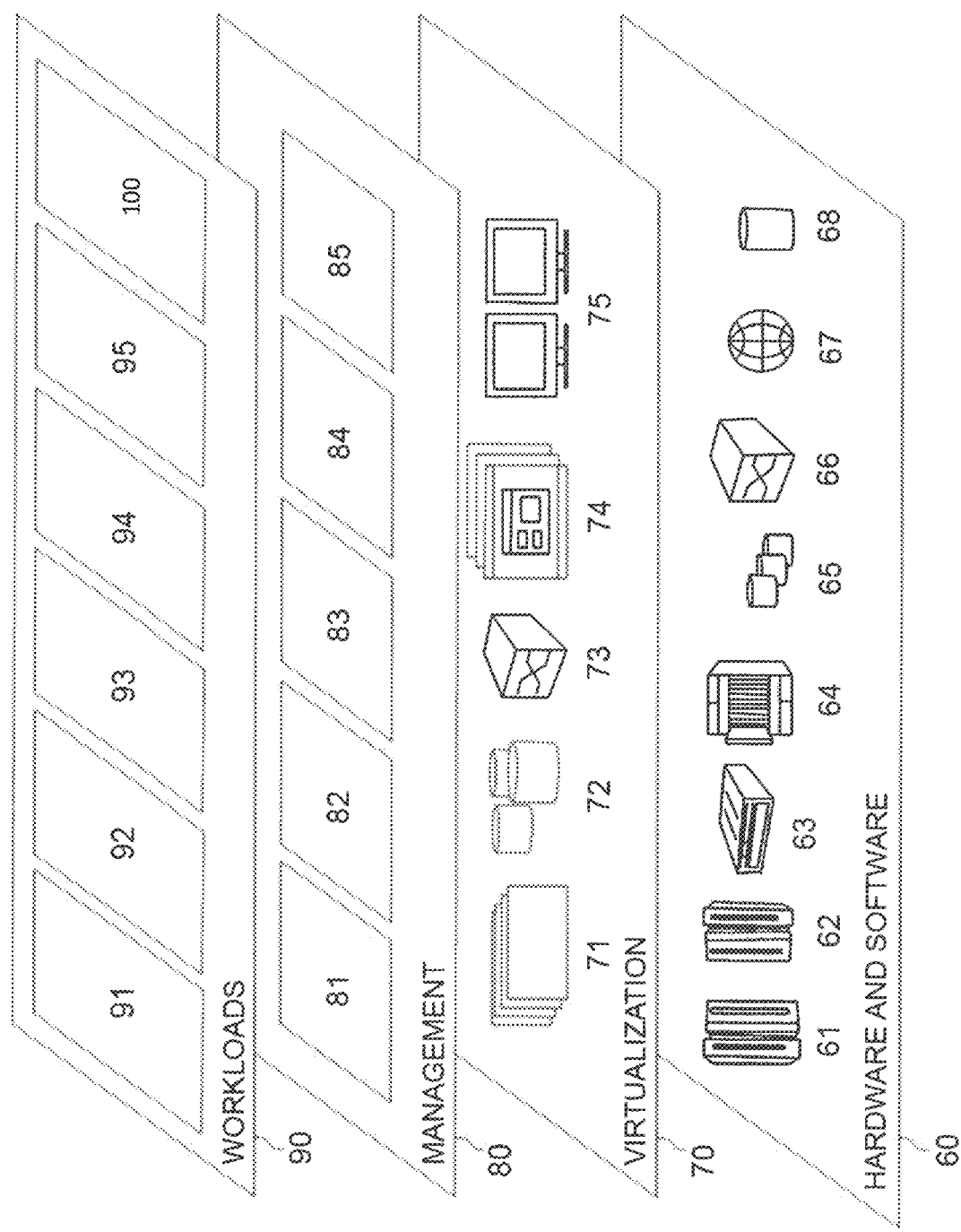
FIG. 9 depicts abstraction model layers according to an embodiment of the present invention.

Referring now to FIG. 9, an exemplary set of functional abstraction layers provided by cloud computing environment 50 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, more particularly relative to the present invention, the Software optimization method 100.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A neural probe apparatus, the apparatus comprising:
   a neural probe; and
   a chip mounted on the neural probe, the chip including:
      a high-density electrode array; and
      a complementary metal-oxide-semiconductor (CMOS) processor, wherein the high-density electrode array comprises:
         a plurality of electrodes, each electrode of the plurality of electrodes includes:
            a top drain;
            a bottom source; and
            a gate, the top drain being on an opposite side of the gate than the bottom source; and
            a top electrode physically coupled to the top drain,
         a wordline physically connected to the gate of each of the plurality of electrodes, each gate of the plurality of electrodes are controlled by a wordline voltage; and
         a bitline physically connected to the bottom source of each of the plurality of electrodes, wherein each electrode of the plurality of electrodes is individually controlled by the wordline and the bitline and accessed via a cross-point.

2. The apparatus of claim 1, wherein the plurality of electrodes are formed on a top of an array of vertical field-effect transistors (FETs).

3. The apparatus of claim 1, wherein each electrode connects to a vertical nanowire field-effect transistor (FET) with a wrap-around gate.

4. The apparatus of claim 1, further comprising:
   a bitline control circuit coupled to the bitline; and
   a wordline control circuit coupled to the wordline that controls the wordline voltage.

5. The apparatus of claim 1, wherein the wordline control circuit and the bitline control circuit individually control the wordline and the bitline.

6. The apparatus of claim 1, wherein the plurality of electrodes are configured as fully compatible with a complementary metal-oxide-semiconductor (CMOS) fabrication.

* * * * *